United States Patent [19]
Sato et al.

[11] 3,960,863

[45] June 1, 1976

[54] PYRIDO[1,2-A]PYRIMIDINONE DERIVATIVES

[75] Inventors: Yasunobu Sato; Hiroshi Fujita; Takagi; Katsuo Kamoshita, all of Tokyo, Japan

[73] Assignee: Sankyo Company Limited, Tokyo, Japan

[22] Filed: June 5, 1975

[21] Appl. No.: 583,864

[30] Foreign Application Priority Data
June 25, 1974 Japan.............................. 49-72549
June 25, 1974 Japan.............................. 49-72550

[52] U.S. Cl. ..................... 260/256.4 F; 260/251 A; 424/251
[51] Int. Cl.² ........................................ C07D 471/04
[58] Field of Search............................ 260/256.4 F

[56] References Cited
UNITED STATES PATENTS
| | | | |
|---|---|---|---|
| 3,299,067 | 1/1967 | Regnier et al. | 260/256.4 N |
| 3,491,097 | 1/1970 | Koppe et al. | 260/268 BC |
| 3,808,212 | 4/1974 | Renth et al. | 260/268 BC |
| 3,887,557 | 6/1975 | Minami et al. | 260/256.4 F |

FOREIGN PATENTS OR APPLICATIONS
621,702  12/1962  Belgium

*Primary Examiner*—Alton D. Rollins
*Assistant Examiner*—James H. Turnipseed
*Attorney, Agent, or Firm*—Flynn & Frishauf

[57] ABSTRACT

3-[2-(4-phenyl-1-piperazinyl)ethyl]-4H-pyrido[1,2-a]pyrimidin-4-one derivatives have central nervous depressant and hypotensive activities and are useful as major tranquillizers.

The compounds can be prepared by (a) reacting 2-methyl-3-halogeno (or arylsulfonyloxy or alkylsulfonyloxy)ethyl-4H-pyrido[1,2-a]pyrimidin-4-one derivative with 1-phenylpiperazine derivative or (b) reacting an aminopyridine with 2-[2-(4-phenyl-1-piperazinyl)ethyl]-acetoacetic acid ester.

8 Claims, No Drawings

PYRIDO[1,2-A]PYRIMIDINONE DERIVATIVES

This invention relates to novel pyrido[1,2-a]-pyrimidinone derivatives and a novel process for the preparation thereof.

More particularly, it relates to pyrido[1,2-a]-pyrimidinone derivatives having the formula

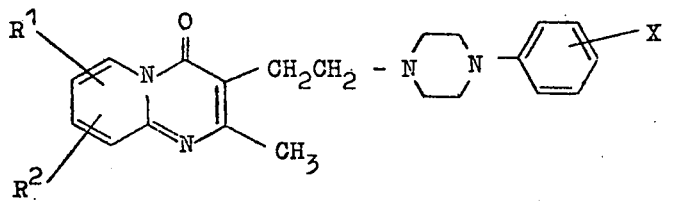

in which $R^1$ and $R^2$ are the same or different, and each represents hydrogen atom, an alkyl group having 1–4 carbon atoms or a halogen atom and may be placed in 6-, 7-, 8- or 9-positions of the pyrido[1,2-a]pyrimidine ring; X represents hydrogen atom, an alkyl group having 1–4 carbon atoms, an alkoxy group having 1–4 carbon atoms, a trifluoromethyl group or a halogen atom, and X may be placed in any positions of the benzene ring and a pharmaceutically acceptable acid addition salt thereof and a process for the preparation thereof.

In the aforementioned general formula (I), $R^1$ and $R^2$ are the same or different, and each preferably represents hydrogen atom, a straight or branched alkyl group having 1–4 carbon atoms, for instance, methyl, ethyl, n-propyl, isopropyl, n-butyl and isobutyl, and a halogen atom, for instance, chlorine, bromine and fluorine. X preferably represents hydrogen atom, a straight or branched alkyl group having 1–4 carbon atoms, for instance, methyl, ethyl, n-propyl, isopropyl, n-butyl and isobutyl, a straight or branched alkoxy group having 1–4 carbon atoms, for instance, methoxy, ethoxy, n-propoxy, isopropoxy, n-butoxy and isobutoxy, trifluoromethyl group, or a halogen atom, for instance, chlorine, bromine and fluorine.

We have earnestly studied on pyridopyrimidine derivatives for many years and have attained this invention upon finding that novel pyrido[1,2-a]pyrimidinone derivatives having the aforementioned general formula (I) show depressant effects on a central nervous system and hyporensive with relatively lower side-effects and are useful as major tranquillizers.

According to the process of this invention, the compound having the aforementioned general formula (I) is prepared by (a) reacting a pyrido[1,2-a]pyrimidine derivative having the general formula

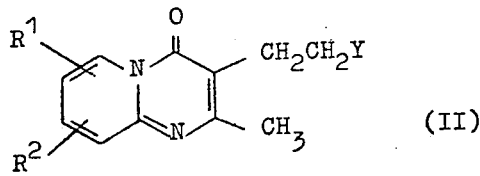

in which $R^1$ and $R^2$ have the same meanings as defined above, and Y represents a halogen atom such as chlorine, bromine and iodine, an arylsulfonyloxy group such as benzenesulfonyloxy and p-toluenesulfonyloxy, or a lower alkylsulfonyloxy group such as methylsulfonyloxy and ethylsulfonyloxy, with a piperazine having the general formula

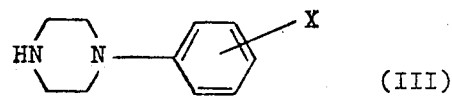

in which X has the same meaning as defined above, or by (b) reacting an aminopyridine derivative having the formula

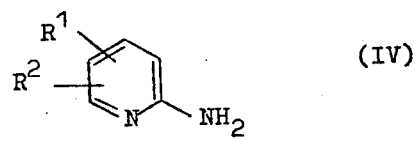

in which $R^1$ and $R^2$ have the same meanings as defined above with a piperazinylethylacetoacetic acid ester having the formula

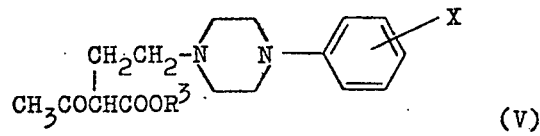

in which X has the same meaning as defined above, and $R^3$ represents a straight or branched lower alkyl group, for instance, methyl, ethyl, n-propyl, isopropyl, n-butyl and isobutyl.

In carrying out the process of this invention, the reaction of the compound (II) with the compound (III) is carried out by bringing the compound having the aforementioned general formula (II) into contact with the compound having the aforementioned general formula (III). The reaction may be carried out in the presence or absence of a solvent, but the use of a solvent is generally preferred so as to perform the reaction smoothly. There is no specific limitation on the solvent used when a solvent is involved, so far as it does not participate in the reaction. As the solvent, there may preferably be mentioned an aromatic hydrocarbon, for instance, benzene and toluene, an alcohol, for instance, ethanol and isopropanol, and a dialkylformamide, for instance, dimethylformamide. There is no specific limitation on the reaction temperature, but the reaction is generally carried out at a temperature ranging from 50° to 200°C. Preferably, the reaction may be performed with heating at a temperature near the reflux temperature of the solvent used. The reaction period may vary depending mainly upon kind of the starting compound, reaction temperature and so on, and is generally about 5 to about 50 hours.

In the present reaction, an acid binding agent such as an inorganic or organic base may be also employed, in addition to the piperazine. As the preferred acid binding agent, there may be mentioned alkai metal carbonates such as sodium carbonate and potassium carbonate and trialkylamines such as triethylamine.

The desired compound may be taken out of the reaction mixture in the usual way, after completion of the reaction. For instance, the desired compound is obtained as crystals through filtration after the reaction and subsequent concentration of the filtrate under reduced pressure. In case of an oily product is obtained, it is converted into its crystalline salt as mentioned below.

The desired compound thus obtained may, if desired, be purified in the usual way, for instance, through recrystallization or column chromatography.

Alternatively, the compound (I) in this invention can be prepared by reacting the compound (IV) with the compound (V). The reaction is carried out by bringing the compound having the aforementioned general formula (IV) into contact with a compound having the aforementioned general formula (V). The reaction may be carried out by using a condensing agent in the presence or absence of a solvent, and an excess amount of the condensing agent is generally employed. There is no specific limitation on the solvent used when a solvent is involved, so far as it does not participate in the reaction. The solvent may preferbly be halogenated hydrocarbons, for instance, chloroform and dichloromethane. The condensing agent may preferably be polyphosphoric acid or a polyphosphoric acid ester. There is no specific limitation on the reaction temperature, but the reaction temperature of 50° to 200°C may generally be employed. The reaction period may vary depending mainly upon the nature of the starting compound, reaction temperature and so on, and is generally about 1 to about 20 hours.

The desired compound may be taken out of the reaction mixture in the usual way, after completion of the reaction. For instance, the desired compound is obtained as crystals through the following process: after completion of the reaction, the reaction mixture is poured into ice-water and made basic by addition of a base and, after extraction with an appropriate organic solvent, the solvent is distilled off from the extract to give the product, and, if an oily product is obtained, it is converted into a crystalline salt.

The desired compounds thus obtained may, if desired, be purified in the usual way, for instance, through recrystallization or column chromatography.

Further, the desired compounds thus obtained may be converted into a pharmaceutically acceptable acid addition salts, for example, by treatment with inorganic or organic acids, e.g., hydrochloric acid, sulfuric acid, oxalic acid, maleic acid, tartaric acid and citric acid.

All of the compounds having the aforementioned general formula (I) show prominent effects on central nervous system and hypotensive effects, according to pharmacological tests.

The results of the pharmacological tests are concretely set out in the following Table 1.

Table 1

| Compound | Anesthesia-potentiating Effect Potentiating Effect of Thiopental-induced Anesthesia $ED_{50}$ (mg/kg p.o.) | Acute Toxicity in mouse $LD_{50}$ (mg/kg p.o. or i.p.) |
| --- | --- | --- |
| 3-[2(4-m-tolyl-1-piperazinyl)ethyl]-2,8-dimethyl-4H-pyrido[1,2-a]pyrimidin-4-one | 0.8(0.47–1.36)* | 480(410–562)*p.o. 100–300 i.p. |
| 3-[2(4-m-chloro-phenyl-1-piperazinyl)-ethyl[-2,8-dimethyl-4H-pyrido[1,2-a]-pyrimidin-4-one | 0.92(0.57–1.47) | 635(575–699)p.o. 100–300 i.p. |
| 3-[2-(4-m-methoxy-phenyl-1-piperazinyl)-ethyl]2,8-dimethyl-4H-pyrido[1,2-a]-pyrimidin-4-one | 0.7(0.45–1.09) | 100–300 i.p. |
| 3-[2-(4-p-chloro-phenyl-1-piperazinyl)-ethyl]2,8-dimethyl-4H-pyrido[1,2-a]pyrimidin-4-one | 2.9(2.0–4.1) | 100–300 i.p. |
| 3-[2-(4-m-tolyl-1-piperazinyl)ethyl]-2,6,8-trimethyl-4H-pyrido[1,2-a]pyrimidin-4-one | 1.7(1.16–2.48) | 100–300 i.p. |
| 3-[2-(4-m-tolyl-1-piperazinyl)ethyl]-2,9-dimethyl-4H-pyrido[1,2-a]pyrimidin-4-one | 1.25(0.5–2.28) | 100–300 i.p. |
| 3-[2-(4-p-tolyl-1- | | |

Table 1-continued

| Compound | Anesthesia-potentiating Effect Potentiating Effect of Thiopental-induced Anesthesia ED$_{50}$ (mg/kg p.o.) | Acute Toxicity in mouse LD$_{50}$ (mg/kg p.o. or i.p.) |
| --- | --- | --- |
| piperazinyl)ethyl]-2,9-dimethyl-4H-pyrido-[1,2-a]pyrimidin-4-one | 1.8(1.38–2.5) | 100–300 i.p. |
| chlorpromazine | 3.5(2.05–5.95) | 245(229–260)p.o. 105(92–120)i.p. |

*95% confidence limits

The pharmacological test was performed in the manner that to a mouse having the body weight of about 25 g was orally administered and, after 30 minutes, given through the vein sodium thiopental in an amount of 30 mg per 1 kg of the body weight, and then the duration time of loss of righting reflux was detected. In the above Table, the value is expressed in ED$_{50}$ value, by which the duration time of loss of righting reflex is prolonged twice as long as that of the control having been given with thiopental only. ED$_{50}$ value was calculated according to the method of Litchfield-Wilcoxon (The Journal of Pharmacology and Experimental Therapeutics, 96, 99, 1949).

Accordingly, the compounds of the aforementioned general formula (I) are useful in the same manner as chlorpromazine as psychotropic drugs showing central nervous system depressant effect. As the administration procedure, there may be mentioned oral administration by the use of tablets, capsules, granules, powders, syrup and the like and parenteral administration through injection. The dosage to be administered may vary depending upon conditions, age, weight and the like, and may be within about 30 to about 500 mg/day for an adult at a time or dividedly in the case of oral administration. In the case of parenteral administration, the dosage of 5 to 50 mg is given at a time through intramuscular injection, subcutaneous injection or intravenous injection.

The process of the present invention will be further concretely illustrated by the following examples.

EXAMPLE 1

2-Methyl-3-[2-(4-m-chlorophenyl-1-piperazinyl)ethyl]-4H-pyrido[1,2-a]pyrimidin-4-one A mixture of 1.1 g of 2-methyl-3-(2-chloroethyl)-4H-pyrido[1,2-a]pyrimidin-4-one, 2.95 g of 1-(m-chlorophenyl)piperazine and 15 ml of toluene was refluxed with heating for 30 hours. After completion of the reaction, the reaction mixture was filtered while hot. The filtrate was concentrated under reduced pressure, and the residue was purified by means of column chromatography using alumina. The product was then recrystallized from a mixture of benzene - n-hexane to give 0.75 g of the desired compound as colorless needles, m.p. 112° – 113°C.

Analysis for $C_{21}H_{23}ON_4Cl$: Calcd. (%): C, 65.87; H, 6.05; N, 14.63; Cl, 9.26. Found (%): C, 66.17; H, 6.04; N, 14.77; Cl, 9.42.

EXAMPLE 2

2-Methyl-3-[2-(4-m-tolyl-1-piperazinyl)ethyl)-4H-pyrido[1,2-a]pyrimidin-4-one mixture containing 2.45 g of 1-(m-tolyl)piperazine in place of the 1-(m-chlorophenyl)piperazine azine used in Example 1 was refluxed with heating for 20 hours. The reaction mixture was then treated in the same manner as in Example 1, and the obtained crude crystals were recrystallized from isopropyl ether to give 0.5 g of the desired compound as colorless powders, m.p. 95.5° – 96.5°C.

Analysis for $C_{22}H_{26}ON_4$: Calcd. (%): C, 72.90; H, 7.23; N, 15.46. Found (%): C, 72.90; H, 7.16; N, 15.63.

EXAMPLE 3

3-[2-(4-m-Chlorophenyl-1-piperazinyl)ethyl]-2,6-dimethyl-4H-pyrido[1,2-a]pyrimidin-4-one A mixture of 2.4 g of 3-(2-chloroethyl)-2,6-dimethy-4H-pyrido[1,2-a]pyrimidin-4-one, 5.9 g of 1-(m-chlorophenyl)piperazine and 25 ml of toluene was refluxed with heating for 30 hours. The reaction mixture was then treated in the same manner as in Example 1, and the obtained crude crystals were recrystallized from isopropyl alcohol to give 1.4 g of the desired compound as pale yellow needles, m.p. 116.5° – 117.5°C.

Analysis for $C_{22}H_{25}ON_4Cl$: Calcd. (%): C, 66.57; H, 6.35; N, 14.12; Cl, 8.93. Found (%): C, 66.88, H, 6.33; N, 14.29; Cl, 9.01.

EXAMPLE 4

3-[22-(-m-Tolyl-1-piperazinyl)ethyl]-2,8-dimethyl-4H-pyrido[1,2-a]pyrimidin-4-one . dihydrochloride A mixture of 2.4 g of 3-(2-chloroethyl)-2,8-dimethyl-4H-pyrido[1,2-a]pyrimidin-4-one, 4.2 g of 1-(m-tolyl)-piperazine and 25 ml of toluene was refluxed for 30 hours. After completion of the reaction, the reaction mixture was filtered, and the filtrate was concentrated under reduced pressure. The obtained residue was purified by means of column chromatography employing alumina. After evaporation of the solvent from the eluate, the residual product was converted into the hydrochloride with ethanolic hydrogen chloride. The obtained hydrochloride was recrystallized from a mixture of methanol and ethanol to give 0.9 g of the desired compound as orange plates, m.p. 267° – 269°C (decomp.).

Analysis for $C_{23}H_{30}ON_4Cl_2 \cdot \frac{1}{2}H_2O$: Calcd. (%): C, 60.26; H, 6.82; N, 12.22; Cl, 15.47. Found (%): C, 60.77; H, 6.58; N, 12.28; Cl, 15.88.

EXAMPLE 5

3-[2-(4-m-Chlorophenyl-1-piperazinyl)ethyl]-2,8-dimethyl-4H-pyrido[1,2-a]pyrimidin-4-one . dihydrochloride A mixture of 2.4 g of 3-(2-chloroethyl)-2,8-dimethyl-4H-pyrido[1,2-a]pyrimidin-4-one, 5.9 g of 1-(m- chlorophenyl)piperazine and 25 ml of toluene was refluxed for 30 hours. After completion of the reaction, the rection mixture was then treated in the same manner as in Example 4, and the obtained crude crystals were recrystallized from a mixture of methanol and ethanol to give 2.2 g of the desired compound as pale yellow plates, m.p. 272° – 274°C (decomp.).

Analysis for $C_{22}H_{27}ON_4Cl_3.H_2O$: Calcd. (%): C, 54.16; H, 6.00; N, 11.48; Cl, 21.80. Found (%): C, 54.52; H, 5.78; N, 11.45; Cl, 22.20.

EXAMPLE 6

3-[2-(4-n-Tolyl-1-piperazinyl)ethyl]-2,9-dimethyl-4H-pyrido[1,2-a]pyrimidin-4-one A mixture of 2.4 g of 3-(2-chloroethyl)-2,9-dimethyl-4H-pyrido[1,2-a]pyrimidin-4-one, 5.3 g of 1-(m-tolyl)-piperazine and 25 ml of toluene was refluxed for 34 hours. After completion of the reaction, the reaction mixture was filtered while hot. The filtrate was concentrated under reduced pressure, and the residue was, after addition of water, extracted with chloroform. The solvent was evaporated from the extract, and the crude crystals were recrystallized from isopropyl ether to give 2.2 g of the desired compound as pale yellow needles, m.p. 106° – 106.5°C.

Analysis for $C_{23}H_{28}ON_4$: Calcd. (%): C, 73.37; H, 7.50; N, 14.88. Found (%): C, 73.23; H, 7.44; N, 15.02.

EXAMPLE 7

3-[2-(4-m-Tolyl-1-piperazinyl)ethyl]-2,6,8-trimethyl-4H-pyrido[1,2-a]pyrimidin-4-one . dihydrochloride A mixture of 2.5 g of 3-(2-chloroethyl)-2,6,8-trimethyl-4H-pyrido[1,2-a]pyrimidin-4-one, 5.3 g of 1-(m-tolyl)piperazine and 20 ml of toluene was refluxed for 24 hours. After completion of the reaction, the reaction mixture was concentrated under reduced pressure, and the obtained residue was purified by means of column chromatography using alumina. The oil obtained from the eluate was converted into the hydrochloride, which was then recrystallized from ethanol to give 0.8 g of the desired compound as pale yellow powders, m.p. 274°C (decomp.).

Analysis for $C_{24}H_{32}ON_4Cl_2.2H_2O$: Calcd. (%): C, 57.71; H, 7.26; N, 11.22; Cl, 14.19. Found (%): C, 57.53; H, 6.83; N, 11.25; Cl, 14.57.

EXAMPLE 8

2-Methyl-3-[2-(4-m-tolyl-1-piperazinyl)ethyl]-7-chloro-4H-pyrido[1,2-a]pyrimidin-4-one A mixture of 1.3 g of 2-methyl-3-(2-chloroethyl)-7-chloro-4H-pyrido[1,2-a]pyrimidin-4-one, 2.1 g of 1-(m-tolyl)piperazine and 20 ml of toluene was refluxed for 30 hours. After completion of the reaction, the reaction mixture was filtered and the filtrate was concentrated under reduced pressure. The obtained residue was purified by means of column chromatography using alumina and recrystallized from a mixture of ethanol and n-hexane to give 0.8 g of the desired compound as pale yellow scales, m.p. 119° – 120°C.

Analysis for $C_{22}H_{25}ON_4Cl$: Calcd. (%): C, 66.57; H, 6.35; N, 14.12; Cl, 8.93. Found (%): C, 66.53; H, 6.50; N, 14.32; Cl, 9.14.

EXAMPLE 9

2-Methyl-3-[2-(4-m-chlorophenyl-1-piperazinyl)ethyl]-7-chloro-4H-pyrido[1,2-a]pyrimidin-4-one A mixture of 1.3 g of 2-methyl-3-(2-chloroethyl)-7-chloro-4H-pyrido[1,2-a]pyrimidin-4-one, 4.2 g of 1-(m-chlorophenyl)piperazine and 20 ml of toluene was refluxed with heating for 30 hours. After completion of the reaction, the reaction mixture was then treated in the same manner as in Example 8. The crude crystals thus obtained were recrystallized from ethanol to give 0.5 g of the desired compound as pale orangeyellow needles, m.p. 152° – 154°C.

Analysis for $C_{21}H_{22}ON_4Cl_2$: Calcd. (%): C, 60.42; H, 5.31; N, 13.42; Cl, 16.99. Found (%): C, 60.20; H, 5.31; N, 13.21; Cl, 17.05.

EXAMPLE 10

3-[2-(4-m-Tolyl-1-piperazinyl)ethyl]-2,7-dimethyl-4H-pyrido[1,2-a]pyrimidin -4-one A mixture of 2.2 g of 3-(2-chloroethyl)-2,7-dimethyl-4H-pyrido[1,2-a]pyrimidin-4-one, 5 g of 1-(m-tolyl)-piperazine and 25 ml of toluene was refluxed for 30 hours. After completion of the reaction, the reaction mixture was filtered while hot and the filtrate was concentrated under reduced pressure. The residue was purified by means of column chromatography using alumina and recrystallized from a mixture of ethanol and isopropyl ether to give 2 g of the desired compound as pale yellow prisms, m.p. 115 – 116°C.

Analysis for $C_{23}H_{28}ON_4$: Calcd. (%): C, 73.37; H, 7.50; N, 14.88. Found (%): C, 73.42; H, 7.35; N, 15.10.

EXAMPLE 11

3-[2-(4-m-Chlorophenyl-1-piperazinyl)ethyl]-2,7-dimethyl-4H-pyrido[1,2-a]pyrimidin-4-one A mixture of 2.2 g of 3-(2-chloroethyl)-2,7-dimethyl-4H-pyrido[1,2-a]pyrimidin-4-one, 4.5 g of 1-(m-chlorophenyl)piperazine and 25 ml of toluene was refluxed for 30 hours. After completion of the reaction, the reaction mixture was then treated in the same manner as in Example 10. The crude crystals thus obtained were recrystallized from a mixture of ethanol and n-hexane to give 1.5 g of the desired compound as pale yellow powders, m.p. 127° – 128°C.

Analysis for $C_{22}H_{25}ON_4Cl$: Calcd. (%): C, 66.57; H, 6.35; N, 14.12. Found (%): C, 66.29; H, 6.32; N, 14.13.

Similarly, the following pyrido[1,2-a]pyrimidinone derivatives were prepared from appropriate starting materials according to the procedure of the foregoing;

2-Methyl-3-[2-(4-phenyl-1-piperaziyl)ethyl]-4H-pyrido-[1,2-a]pyrimidin-4-one . trihydrochloride m.p. 260°C (decomp.)

Analysis for $C_{21}H_{27}ON_4Cl_3.2H_2O$: Calcd. (%): C, 51.07; H, 6.33; N, 11.34; Cl, 21.54. Found (%): C, 51.22; H, 6.38; N, 10.99; Cl, 22.01.

2-Methyl-3-[2-(4-o-chlorophenyl-1-piperazinyl)ethyl]-4H-pyrido[1,2-a]pyrimidin-4-one m.p. 185° – 186°C Analysis for $C_{21}H_{23}ON_4Cl$: Calcd. (%): C, 65.87; H, 6.05; N, 14.63; Cl, 9.26. Found (%): C, 66.23; H, 6.07; N, 14.53; Cl, 9.19.

2-Methyl-3-[2-(4-p-chlorophenyl-1-piperazinyl)ethyl]-4H-pyrido[1,2-a]pyrimidin-4one m.p. 159° – 160°C Analysis for $C_{21}H_{23}ON_4Cl$: Calcd. (%): C, 65.87; H, 6.05; N, 14.63; Cl, 9.26. Found (%): C, 65.84; H, 5.91; N, 14.76; Cl, 9.31.

2-Methyl-3-[2-(4-o-tolyl-1-piperazinyl)ethyl]-4H-pyrido-[1,2-a]pyrimidin-4-one m.p. 151° – 152°C Analysis for $C_{22}H_{26}ON_4$: Calcd. (%): C, 72.90; H, 7.23; N, 15.46. Found (%): C, 72.84; H, 7.18; N, 15.40.

2-Methyl-3-[2-(4-p-tolyl-1-piperazinyl)ethyl]-4H-pyrido-[1,2-a]pyrimidin-4-one m.p. 124° – 126°C Analysis for $C_{22}H_{26}ON_4$: Calcd. (%): C, 72.90; H, 7.23; N, 15.46. Found (%): C, 72.74; H, 7.15; N, 15.46.

2-Methyl-3-{2-[4-(m-trifluoromethylphenyl)-1-piperazinyl]-ethyl}-4Hpyrido[1,2-a]pyrimidin-4-one . dihydrochloride m.p. 245°C (decomp.)

Analysis for $C_{22}H_{25}ON_4Cl_2F_3 \cdot H_2O$: Calcd. (%): C, 52.07; H, 5.36; N, 11.04; Cl, 13.97. Found (%): C, 51.74; H, 5.61; N, 11.33; Cl, 14.01.

3-[2-(4-o-Chlorophenyl-1-piperazinyl)ethyl]-2,6-dimethyl-4Hpyrido[1,2-a]pyrimidin-4-one m.p. 147° – 148°C Analysis for $C_{22}H_{25}ON_4Cl$: Calcd. (%): C, 66.57; H, 6.35; N, 14.12; Cl, 8.93. Found (%): C, 66.77; H, 6.27; N, 14.22; Cl, 9.06.

3-[2-(4-p-Chlorophenyl-1-piperaziiyl)ethyl]-2,6-dimethyl-4H-pyrido[1,2-a]pyrimidin-4-one m.p. 157° – 158°C Analysis for $C_{22}H_{25}ON_4Cl$: Calcd. (%): C, 66.57; H, 6.35; N, 14.12; Cl, 8.93. Found (%): C, 66.63; H, 6.47; N, 13.89; Cl, 8.93.

3-[2-(4-Phenyl-1-piperazinyl)ethyl]-2,8-dimethyl-4H-pyrido[1,2-a]pyrimidin-4-one m.p. 126° – 127°C Analysis for $C_{22}H_{26}ON_4$: Calcd. (%): C, 72.90; H, 7.23; N, 15.46. Found (%): C, 72.24; H, 7.29; N, 15.38.

3-[2-(4-p-Tolyl-1-piperazinyl)ethyl]-2,8-dimethyl-4H-pyrido[1,2-a]pyrimidin-4-one m.p. 162.5° – 163.5°C Analysis for $C_{23}H_{28}ON_4$: Calcd. (%): C, 73.37; H, 7.50; N, 14.88. Found (%): C, 73.32; H, 7.45; N, 14.96.

3-[2-(4-o-Tolyl-1-piperazinyl)ethyl]-2,8-dimethyl-4H-pyrido[1,2-a]pyrimidin-4-one m.p. 141° – 142°C Analysis for $C_{23}H_{28}ON_4$: Calcd. (%): C, 73.37; H, 7.50; N, 14.88. Found (%): C, 73.46; H, 7.51; N, 14.81.

3-[2-(4-p-Chlorophenyl-1-piperazinyl)ethyl]-2,8-dimethyl-4H-pyrido[1,2-a]pyrimidin-4-one m.p. 156° – 157°C Analysis for $C_{22}H_{25}ON_4Cl$: Calcd. (%): C, 66.57; H, 6.35; N, 14.12; Cl, 8.93. Found (%): C, 66.60; H, 6.37; N, 13.88; Cl, 8.96.

3-[2-(4-o-Methoxyphenyl-1-piperazinyl)ethyl]-2,8-dimethyl-4H-pyrido[1,2-a]pyrimidin-4-one m.p. 132° – 133°C Analysis for $C_{23}H_{28}O_2N_4$: Calcd. (%): C, 70.38; H, 7.19; N, 14.28. Found (%): C, 70.21; H, 7.07; N, 14.29.

3-[2-(4-m-Chlorophenyl-1-piperazinyl)ethyl]-2,6,8-trimethyl-4Hpyrido[1,2-a]pyrimidin-4-one . dihydrochloride m.p. above 250°C Analysis for $C_{23}H_{29}ON_4Cl_3 \cdot 2H_2O$: Calcd. (%): C, 53.13; H, 6.40; N, 10.77; Cl, 20.46. Found (%): C, 52.50; H, 6.39; N, 10.07; Cl, 20.52.

3-[2-(4-o-Chlorophenyl)-1-piperazinyl]-2,8-dimethyl-4H-pyrido[1,2-a]pyrimidin-4-one m.p. 157° – 158°C Analysis for $C_{22}H_{25}ON_4Cl$: Calcd. (%): C, 66.57; H, 6.35; N, 14.12; Cl, 8.93. Found (%): C, 66.64; H, 6.06; N, 13.82; Cl, 8.97.

3-[2-(4-m-Chlorophenyl-1-piperazinyl)ethyl]-2,9-dimethyl-4H-pyrido[1,2-a]pyrimidin-4-one . dihydrochloride m.p. 236° – 238°C (decomp.)

Analysis for $C_{22}H_{27}ON_4Cl_3 \cdot H_2O$: Calcd. (%): C, 54.16; H, 5.99; N, 11.48; Cl, 21.80. Found (%): C, 54.28; H, 6.06; N, 11.23; Cl, 21.82.

3-[2-(4-m-Tolyl-1-piperazinyl)ethyl]-2,6-dimethyl-4H-pyrido[1,2-a]pyrimidin-4-one . dihydochloride m.p. 162° – 164°C (decomp.)

Analysis for $C_{23}H_{30}ON_4Cl_2 \cdot 2H_2O$: Calcd. (%): C, 56.90; H, 7.06; N, 11.54. Found (%): C, 56.39; H, 7.11; N, 11.55.

3-[2-(4-Phenyl-1-piperazinyl)ethyl]-2,7-dimethyl-4H-pyrido[1,2-a]pyrimidin-4-one m.p. 146° – 147°C Analysis for $C_{22}H_{26}ON_4$: Calcd. (%): C, 72.90; H, 7.23; N, 15.46. Found (%): C, 72.49; H, 7.04; N, 15.42.

3-[2-(4-m-Methoxyphenyl-1-piperazinyl)ethyl]-2,8-dimethyl-4H-pyrido[1,2-a]pyrimidin-4-one m.p. 120° – 121°C Analysis for $C_{23}H_{28}O_2N_4$: Calcd. (%): C, 70.38; H, 7.19; N, 14.28. Found (%): C, 70.27; H, 7.09; N, 14.02.

3-[2-(4-p-Tolyl-1-piperazinyl)ethyl]-2,9-dimethyl-4H-pyrido[1,2-a]pyrimidin-4-one m.p. 153° – 154°C Analysis for $C_{23}H_{28}ON_4$: Calcd. (%): C, 73.37; H, 7.50; N, 14.88. Found (%): C, 73.40; H, 7.57; N, 14.69.

3-[2-(4-p-Chlorophenyl-1-piperazinyl)ethyl]-2,9-dimethyl-4H-pyrido[1,2-a]pyrimidin-4-one m.p. 141° – 142°C Analysis for $C_{22}H_{25}ON_4Cl$: Calcd. (%): C, 66.57; H, 6.35; N, 14.12; Cl, 8.93. Found (%): C, 66.92; H, 6.51; N, 13.96; Cl, 8.97.

3-[2-(4-p-Tolyl-1-piperazinyl)ethyl]-2,7-dimethyl-4H-pyrido[1,2-a]pyrimidin-4-one m.p. 182° – 184°C Analysis for $C_{23}H_{28}On_4$: Calcd. (%): C, 73.37; H, 7.50; N, 14.88. Found (%): C, 73.02; H, 7.34; N, 14.76.

3-[2-(4-p-Methoxyphenyl-1-piperazinyl)ethyl]-2,8-dimethyl-4H-pyrido[1,2-a]pyrimidin-4-one m.p. 136° – 137°C Analysis for $C_{23}H_{28}O_2N_4$: Calcd. (%): C, 70.38; H, 7.19; N, 14.28. Found (%): C, 70.44; H, 7.25; N, 14.19.

3-[2-(4-p-Tolyl-1-piperazinyl)ethyl]-2,6,8-trimethyl-4H-pyrido[1,2-a]pyrimidin-4-one m.p. 111° – 112°C Analysis for $C_{24}H_{30}ON_4$: Calcd. (%): C, 73.81; H, 7.74; N, 14.35. Found (%): C, 73.63; H, 7.76; N, 14.07.

3-[2-(4-p-chlorophenyl-1-piperazinyl)ethyl]-2,6,8-trimethyl-4H-pyrido[1,2-a]pyrimidin-4-one m.p. 119° – 121°C Analysis for $C_{23}H_{27}ON_4Cl$: Calcd. (%): C, 67.22; H, 6.62; N, 13.63; Cl, 8.63. Found (%): C, 66.95; H, 6.60; N, 13.46; Cl, 8.74.

EXAMPLE 12

3-[2-(4-m-Chlorophenyl-1-piperazinyl)ethyl]-2,8-dimethyl-4H-pyrido[1,2-a]pyrimidin-4-one . dihydrochloride In 5 ml of pyridine was suspended 2 g of 3-(2-hydoxyethyl)-2,8-dimethyl-4H-pyido[1,2-a]pyrimidin-4one, and 2.7 g of p-toluenesulfonic acid chloride was added thereto. After dissolution by heating, the mixture was stirred at room temperature for 3 hours. After completion of the reaction, the reaction mixture was poured into ice-water and salted out with sodium chloride. The precipitated crystals were collected by filtration and recrystallized from a mixture of tetrahydrofuran and isopropyl ether to give 2.15 g of 3-(2-tosyloxyethyl)-2,8-dimethyl-4H-pyrido[1,2-a]pyrimidin-4-one as colorless needles, m.p. 127.5° – 128°C.

A mixture of 1 g of the compound thus obtained, 1.6 g of 1-(m-chlorophenyl)piperazine and 10 ml of toluene was refluxed for one hour with stirring. After completion of the reaction, the reaction mixture was poured into ice-water and extracted with chloroform. The chloroform portion was dried over anhydrous sodium sulfate. The solvent was evaporated from the extract, and the residue was then purified by means of column chromatography using silica gel. The oil obtained from the eluate was converted into the hydrochloride and recrystallized from ethanol to give 0.55 g of the desired compound as pale yellow scales, m.p. 272° – 274°C (decomp.). IR spectrum of the product was identical to that of the product obtained in Example 5.

Similarly, 3-[2-(4-p-chlorophenyl-1-piperazinyl)ethyl]-2,8-dimethyl-4H-pyrido[1,2-a]pyrimidin-4-one (m.p. 156° – 157°C) and 3-[2-(4-m-tolyl-1-piperazinyl)ethyl]-2,8-dimethyl-4H-pyrido[1,2-a]pyrimidin-4-one (m.p. 96° – 97°C) were obtained from the appropriate starting materials according to the procedure of the Example 12.

EXAMPLE 13

3-[2-(4-m-Tolyl-1-piperazinyl)ethyl]-2,8-dimethyl-4H-pyrido[1,2-a]pyrimidin-4-one . dihydrochloride A mixture of 0.19 g of 4-methyl-2-aminopyridine, 1 g of ethyl 2-[2-(4-m-tolyl-1-piperazinyl)ethyl]acetoacetate and 1.17 g of polyphosphoric acid was heated at 140° – 150°C for 2 hours. After completion of the reaction, water was added to the reaction mixture. The resulting mixture was made basic by addition of an aqueous sodium hydroxide solution and then extracted with ethyl acetate. After evaporation of the solvent from the extract, the remaining residue was purified by means of column chromatography employing alumina. The product was then converted into its hydrochloride by ethanolic hydrogen chloride and recrystallized from ethanol to give 0.25 g of the desired compound as pale orangeyellow plates, m.p. 267° – 269°C (decomp.).

Analysis for $C_{23}H_{30}ON_4Cl_2 . \frac{1}{2}H_2O$: Calcd. (%): C, 60.26; H, 6.82; N, 12.22; Cl, 15.47. Found (%): C, 60.51; H, 6.71; N, 12.60; Cl, 15.70.

Similarly, the following pyrido[1,2-a]pyrimidinone derivatives were prepared from appropriate starting materials according to the procedure of the foregoing;

3-[2-(4-m-Chlorophenyl-1-piperazinyl)ethyl]-2,8-dimethyl-4H-pyrido[1,2-a]pyrimidin-4-one . dihydrochloride
  m.p. 272° – 274°C (decomp.)

3-[2-(4-m-Tolyl-1-piperazinyl)ethyl]-2,6,8-trimethyl-4H-pyrido[1,2-a]pyrimidin-4-one . dihydrochloride
  m.p. 274°C (decomp.)

2-Methyl-3-[-2-(4-phenyl-1-piperazinyl)ethyl]-4-pyrido[1,2-a]pyrimidin-4-one . trihydrochloride
  m.p. 260°C (decomp.)

3-[2-(4-m-Chlorophenyl-1-piperazinyl)ethyl]-2,6,8-trimethyl-4H-pyrido[1,2-a]pyrimidin-4-one . dihydrochloride
  m.p. above 270°C 3-[2-(4-m-Chlorophenyl-1-piperazinyl)ethyl]-2,9-dimethyl-4H-pyrido[1,2-a]pyrimidin-4-one . dihydrochloride
  m.p. 236° – 238°C 3-[2-(4-m-Tolyl-1-piperazinyl)ethyl]-2,6-dimethyl-4H-pyrido[1,2-a]pyrimidin-4-one . dihydrochloride
  m.p. 162° – 164°C

EXAMPLE 14

3-[2-(4-m-Tolyl-1-piperazinyl)ethyl]-2,9-dimethyl-4H-pyrido[1,2-a]pyrimidin-4-one A mixture of 0.19 g of 3-methyl-2-aminopyridine, 1 g of ethyl 2-[2-(4-m-tolyl-1-piperazinyl)ethyl]acetoacetate and 1.17 g of polyphosphoric acid was heated at 120° – 130°C for 2 hours. After completion of the reaction, water was added to the reaction mixture. The resulting mixture was made basic by addition of an aqueous sodium hydroxide solution and then extracted with ethyl acetate. After evaporation of the solvent from the extract, the remaining residue was washed with isopropyl alcohol and recrystallized from isopropyl alcohol to give 0.1 g of the desired compound as pale yellow needles, m.p. 106° – 106.5°C.

Analysis for $C_{23}H_{28}ON_4$: Calcd. (%): C, 73.37; H, 7.50; N, 14.88. Found (%): C, 73.60; H, 7.80; N, 15.11.

Similarly, the following pyrido[1,2-a]pyrimidinone derivatives were prepared from appropriate starting materials according to the procedure of the foregoing;

3-[2-(4-o-Methoxyphenyl-1-piperazinyl)ethyl]-2,8-dimethyl-4H-pyrido[1,2-a]pyrimidin-4-one
  m.p. 132° – 133°C 2-Methyl-3-[2-(4-m-tolyl-1-piperazinyl)ethyl]-7-chloro-4H-pyrido[1,2-a]pyrimidin-4-one
  m.p. 119° – 120°C 2-Methyl-3-[2-(4-m-chlorophenyl-1-piperazinyl)ethyl]-7-chloro-4H-pyrido[1,2-a]pyrimidin-4-one
  m.p. 152° – 154°C 3-[2-(4-p-Chlorophenyl-1-piperazinyl)ethyl[-2,8-dimethyl-4H-pyrido[1,2-a]pyrimidin-4-one
  m.p. 147° – 148°C 3-[2-(4-m-Tolyl-1-piperazinyl)ethyl]-2,9-dimethyl-4H-pyrido[1,2-a]pyrimidin-4-one
  m.p. 106° – 106.5°C 3-[2-(4-o-Tolyl-1-piperazinyl)ethyl[-2,8-dimethyl-4H-pyrido[1,2-a]pyrimidin-4-one
  m.p. 141° – 142°C 2-Methyl-3-[2-(4-p-tolyl-1-piperazinyl)ethyl]-4H-pyrido[1,2-a]pyrimidin-4-one
  m.p. 124° – 126°C 3-[2-(4-m-Tolyl-1-piperazinyl)ethyl]-2,7-dimethyl-4H-pyrido[1,2-a]pyrimidin-4-one
  m.p. 115° – 116°C 3-[2-(4-o-Chlorophenyl-1-piperazinyl)ethyl]-2,8-dimethyl-4H-pyrido[1,2-a]pyrimidin-4-one
  m.p. 157° – 158°C
3-[2-(4-m-Chlorophenyl-1-piperazinyl)ethyl]-2,8-dimethyl-4H-pyrido[1,2-a]pyrimidin-4-one
  m.p. 127° – 128°C

What is claimed is:

1. Pyrido[1,2-a]pyrimidinone derivative having the formula

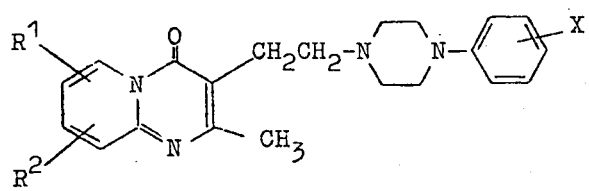

wherein R¹ and R² may be the same or different and each represents a hydrogen atom, an alkyl group having from 1 to 4 carbon atoms or a halogen atom and X represents a hydrogen atom, an alkyl group having from 1 to 4 carbon atoms, an alkoxy group having from 1 to 4 carbon atoms, trifluoromethyl group or a halogen atom and a pharmaceutically acceptable acid addition salt thereof.

2. 3-[2-(4-m-Tolyl-1-piperazinyl)ethyl]-2,8-dimethyl-4H-pyrido[1,2-a]pyrimidin-4-one.

3. 3-[2-(4-m-Chlorophenyl-1-piperazinyl)ethyl]-2,8-dimethyl-4H-pyrido[1,2-a]pyrimidin-4-one.

4. 3-[2-(4-m-Methoxyphenyl-1-piperazinyl)ethyl]-2,8-dimethyl-4H-pyrido[1,2-a]pyrimidin-4-one.

5. 3-[2-(4-p-Chlorophenyl-1-piperazinyl)ethyl]-2,8-dimethyl-4H-pyrido[1,2-a]pyrimidin-4-one.

6. 3-[2-(4-m-Tolyl-1-piperazinyl)ethyl]-2,6,8-trimethyl-4H-pyrido[1,2-a]pyrimidin-4-one.

7. 3-[2-(4-m-Tolyl-1-piperazinyl)ethyl]-2,9-dimethyl-4H-pyrido[1,2-a]pyrimidin-4-one.

8. 3-[2-(4-p-Tolyl-1-piperazinyl)ethyl]-2,9-dimethyl-4H-pyrido[1,2-a]pyrimidin-4-one.

* * * * *

PAGE ONE OF TWO PAGES

UNITED STATES PATENT AND TRADEMARK OFFICE
CERTIFICATE OF CORRECTION

PATENT NO. : 3,960,863
DATED : June 1, 1976
INVENTOR(S) : YASUNOBU SATO et al

It is certified that error appears in the above-identified patent and that said Letters Patent are hereby corrected as shown below:

Title page, at "Inventors": replace "Takagi" with
--- Hiromu Takagi ---.

Column 3, line 18: replace "alkai" with --- alkali ---.

Column 4, line 5: replace "preferbly" with --- preferably ---.

Column 4, Table 1, first column: delete "4-one" from the second compound; --- 4-one --- should be inserted at the end of the _first_ compound.

Column 4, Table 1, second column: after "1.25", replace "(0.5-" with --- (0.54- ---.

Column 5, line 19: replace "reflux" with --- reflex ---.

Column 5, penultimate line: before "mixture", insert --- The --- and begin a new paragraph.

Column 5, last line: delete "azine".

Column 6, line 28: replace "dimethy-" with --- dimethyl ---.

Column 6, line 42: replace "3-[22-(-m-Tolyl-" with --- 3-[2-(4-m-Tolyl- ---.

UNITED STATES PATENT AND TRADEMARK OFFICE
CERTIFICATE OF CORRECTION

PATENT NO. : 3,960,863
DATED : June 1, 1976
INVENTOR(S) : YASUNOBU SATO et al

It is certified that error appears in the above-identified patent and that said Letters Patent are hereby corrected as shown below:

Column 7, line 3: replace "rection" with --- reaction ---.

Column 7, line 14: before "Tolyl", replace "n" with --- m ---.

Column 7, line 25: replace "recyrstallized" with --- recrystallized ---.

Column 8, line 55: replace "piperaziyl" with --- piperazinyl ---.

Column 9, line 30: replace "piperaziiyl" with --- piperazinyl ---.

Column 10, line 19: replace "dihydochloride" with --- dihydrochloride ---.

Column 11, line 11: replace "pyido" with --- pyrido ---.

Column 13, line 4: replace "2,8" with --- 2,7 ---.

Signed and Sealed this

Sixteenth Day of November 1976

[SEAL]

Attest:

RUTH C. MASON
Attesting Officer

C. MARSHALL DANN
Commissioner of Patents and Trademarks